(12) United States Patent
Lupin et al.

(10) Patent No.: US 7,722,524 B2
(45) Date of Patent: May 25, 2010

(54) SURGICALLY IMPLANTABLE HEARING AID

(75) Inventors: Alan J. Lupin, Victoria (CA); Ewa J. Lupin, Victoria (CA)

(73) Assignee: No. 182 Corporate Ventures Ltd., Vancouver, BC (CA)

( * ) Notice: Subject to any disclaimer, the term of this patent is extended or adjusted under 35 U.S.C. 154(b) by 1272 days.

(21) Appl. No.: 11/238,984

(22) Filed: Sep. 30, 2005

(65) Prior Publication Data
US 2006/0025648 A1 Feb. 2, 2006

Related U.S. Application Data

(63) Continuation-in-part of application No. 10/316,066, filed on Dec. 11, 2002, now Pat. No. 7,033,313.

(51) Int. Cl.
*H04R 25/00* (2006.01)
(52) U.S. Cl. ...................................................... 600/25
(58) Field of Classification Search .................. 600/25; 128/897, 898; 381/312, 317
See application file for complete search history.

(56) References Cited

U.S. PATENT DOCUMENTS

| | | | |
|---|---|---|---|
| 2,402,392 A | 6/1946 | Goldschmidt | |
| 4,606,329 A | 8/1986 | Hough | |
| 4,612,915 A * | 9/1986 | Hough et al. | .................. 600/25 |
| 4,982,434 A | 1/1991 | Lenhardt et al. | |
| 4,988,333 A | 1/1991 | Engebretson et al. | |
| 5,047,994 A * | 9/1991 | Lenhardt et al. | ............. 367/116 |
| 5,558,618 A | 9/1996 | Maniglia | |
| 5,772,575 A | 6/1998 | Lesinski et al. | |
| 5,800,336 A | 9/1998 | Ball et al. | |
| 5,859,916 A | 1/1999 | Ball et al. | |
| 6,277,148 B1 | 8/2001 | Dormer | |
| 6,354,299 B1 * | 3/2002 | Fischell et al. | ............... 128/899 |
| 6,358,281 B1 * | 3/2002 | Berrang et al. | ................. 623/10 |
| 6,377,693 B1 * | 4/2002 | Lippa et al. | ................. 381/71.6 |
| 6,394,969 B1 * | 5/2002 | Lenhardt | ........................ 601/2 |
| 6,840,919 B1 * | 1/2005 | Håkansson | ................... 604/175 |
| 7,033,313 B2 * | 4/2006 | Lupin et al. | .................... 600/25 |
| 2001/0003788 A1 | 6/2001 | Ball et al. | |
| 2002/0173697 A1 | 11/2002 | Lenhardt | |
| 2004/0032962 A1 | 2/2004 | Westerkull | |

FOREIGN PATENT DOCUMENTS

EP  0 263 254 A  4/1988

OTHER PUBLICATIONS

Sichel, J-Y., New Approach for Implantable Hearing Aids: A Feasibility Study, Annals of Otology, Rhinology and Laryngology 2004:236-940.

* cited by examiner

*Primary Examiner*—Samuel G Gilbert
(74) *Attorney, Agent, or Firm*—Oyen Wiggs Green & Mutala LLP (57) ABSTRACT

The invention comprises a surgically implantable hearing aid for hearing impaired persons. The hearing aid includes a vibrational element which is vibrated by sound waves and attached to the skull of the person, and a connector which crosses the mastoid cavity and delivers the sound waves to the dura mater of the human being thereby vibrating the dura mater, the cerebrospinal fluids, and the brain to create a hearing percept. The invention can also be adapted to act as a tinnitus masker or used in conjunction with a cochlear implant. It can also be used in a modified form to connect directly through the skull of the human being.

5 Claims, 10 Drawing Sheets

Fig 1b  PLAN VIEW

Fig 1a  SIDE VIEW

SURGICALLY IMPLANTABLE HEARING AID

CROSS REFERENCE TO RELATED APPLICATION

This application is a continuation-in-part of application Ser. No. 10/316,066 filed Dec. 11, 2002.

FIELD OF THE INVENTION

The invention relates to a surgically implantable hearing aid to treat persons with deafness, partial deafness, tinnitus or a combination of these ailments. More particularly, this invention pertains to a surgically implantable hearing aid that stimulates the inner ear by imparting vibrations that correspond to external sounds to the dura mater of the person. The invention is also directed at a method for treating deafness, partial deafness, tinnitus or a combination of these ailments.

BACKGROUND OF THE INVENTION

Hearing loss occurs in approximately one in ten North Americans and in approximately one in ten of these persons, it is classified as profound.

Tinnitus or "ringing" noises in the ears are perceived by about 20% of the population in North America. Approximately 1 million persons in the U.S. alone are experiencing sufficiently severe tinnitus that it impairs their ability to cope with daily life.

Hearing aids for deaf persons have been getting smaller and their function has improved with advances in technology. Great changes have occurred over the years, advancing from the nineteenth century "ear trumpet" to small devices which fit in the ear canal and are not visible externally. A logical development is to implant the aid surgically.

A number of patents are relevant or of interest. Ball et al. in U.S. Pat. No. 5,800,336, describe a "floating mass transducer" with an electromagnet attached to one of the middle ear bones, the incus, such that it drives the ossicular chain. U.S. Pat. No. 5,558,618, Magnilia, describes a device consisting of a magnet mounted to the ossicular chain driven by an implanted electromagnetic coil. Dormer, in U.S. Pat. No. 6,277,148, describes a middle ear magnet driven by a coil placed in the external auditory canal, Leysieffer et al., in U.S. Pat. No. 5,772,575, describe another vibrating piezoelectric device for direct stimulation of the ossicles, Lenhardt et al., in U.S. Pat. No. 5,047,994, describe a device that takes external sound waves and transmits corresponding mechanical vibrations to the human skull.

Most surgically implantable hearing aids suffer among other things from the disadvantage that they involve altering or connection to the ossicles or small bones of the middle ear. These bones are very fragile with tenuous blood supply, and pressure on these ossicles from any direction leads to halisterisis or dissolving of the bone at the point of attachment. This phenomenon occurs either immediately or over a short period of time.

A second disadvantage of implantable hearing aids that connect to the ossicles is that the surgery is complicated and delicate, and admits the possibility of damage to the middle ear membranes, or to the ossicular blood supply or to adjacent structures such as the facial nerve.

A third disadvantage of implantable hearing aids that connect to the ossicles is that the production of vibratory forces via the ossicles or through the middle ear causes sound to exit the ear via the tympanic membrane. This frequently gives rise to auditory feedback or "squealing" which is familiar to users of in-the-ear hearing aids.

There exist other implantable hearing aids that do not involve connection to the ossicles and instead impart mechanical vibrations directly to the skull. Bone anchored hearing aids suffer from the disadvantage that they require insertion in and osseointegration with bone. Because of this, implantation of bone anchored hearing aids is difficult in pediatric patients whose skull bones are thin, soft, immature or malformed.

There is thus a strong need for a hearing aid device that does not damage the middle ear or ossicles; can be implanted surgically with minimum damage to the surrounding structures, for example the facial nerve; which, by design, does not cause auditory feedback; and which does not vibrate the skull by contact insertion.

Tinnitus maskers are devices that produce a sound external to the sufferer and distract the sufferer from hearing the internal noise that is currently believed to be in the brain itself. In this respect, this device could be affected electronically to produce a percept for masking tinnitus in human beings.

The use of an implantable aid with a cochlear implant is becoming more common as new cochlear implant surgical techniques frequently use gentle surgery that leaves existing hearing intact.

SUMMARY OF THE INVENTION

The invention comprises a surgically implantable hearing aid for hearing impaired mammals, such as human beings. The hearing aid includes a vibrational element attached to the skull of the mammal by a bracket, a member which crosses the skull or mastoid cavity and imparts vibrations to the dura mater of the mammal thereby vibrating the dura mater, fluids inside the skull, the brain, and the inner ear to create a hearing percept. The invention can also be adapted to act as a tinnitus masker or used in conjunction with a cochlear implant. It can also be used in a modified form to connect straight through the skull of the mammal.

In one embodiment, the invention relates to a device which can be implanted in the head of a mammal, such as a human being, and can impart vibrations corresponding to sound waves external to the head to the dura mater of the mammal.

In another embodiment, the invention relates to a device which can be implanted in the head of a mammal, such as a human being, and can impart vibrations corresponding to sound waves external to the head to a moveable bone disc cut from the skull that can impinge the dura mater of the mammal.

In another embodiment, the invention relates to a device that can be implanted in the head of a human being and comprises a sound wave receiving microphone which converts the sound waves into electrical signals and transmits the electrical signals to a transducer, a transducer which converts the electrical signals to mechanical vibrations, and a member which transmits mechanical vibrations from the transducer to the dura mater or to a floating bone disc that can impinge on the dura mater.

In another embodiment the invention relates to a device that can be combined with electronics that make it possible for an implanted portion of the device to transcutaneously communicate power and data with an external portion of the device across the intact skin of the head of a human being. Said electronics might include one or more transcutaneous energy transfer coils; one or more wireless data receivers, one or more wireless data transmitters; electronics for signal processing; switches; and an energy storage element, such as a battery.

Embodiments of the invention can be used as hearing aids or as tinnitus maskers. Embodiments of the invention can be used in association with a cochlear implants. Embodiments of the invention can be used in both ears of the person as a bilateral aid to hearing.

In one embodiment, the invention also relates to a surgically implantable apparatus comprising: (a) a microphone which receives sound waves and converts them to electrical signals; (b) a transducer which converts the electric signals to produce mechanical vibrations driven either electromagnetically, piezoelectrically, magnetostrictively, electrostrictively or by other means; (c) a bracket which attaches to the skull of a human being over the mastoid cavity and supports transducer; and, (d) a member which transfers the mechanical vibrations from the transducer to the dura mater of the interior of the skull of a human being.

The invention is also directed to a method for treating deafness or partial deafness in a human being. In one embodiment the method comprises transmitting vibrations to the human being's dura mater, wherein the vibrations correspond to sound waves external to the head of the human being. In a further embodiment, the method comprises transmitting vibrations to a bone disc resting on the human being's dura mater, wherein the vibrations correspond to sound waves external to the head of the human being. In yet a further embodiment, the method comprises coupling a transducer which converts electrical signals into mechanical vibrations to the human being's dura mater, converting sound waves external to the head of the human being into electrical signals, and transmitting the electrical signals to the transducer. In still a further embodiment the method comprises coupling a transducer which converts electrical signals into mechanical vibrations to a bone disc resting on the human being's dura mater, converting sound waves external to the head of the human being into electrical signals, and transmitting the electrical signals to the transducer.

The invention is also directed to a method for masking tinnitus in a human being. In one embodiment the method comprises transmitting vibrations to the human being's dura mater. In a further embodiment the method comprises transmitting vibrations to a bone disc resting on the human being's dura mater. In yet a further embodiment the method comprises coupling a transducer which converts electrical signals into mechanical vibrations to the human being's dura mater, generating electrical signals, and transmitting the electrical signals to the transducer. In still a further embodiment the method comprises coupling a transducer which converts electrical signals into mechanical vibrations to a bone disc resting on the human being's dura mater, generating electrical signals and transmitting the electrical signals to the transducer.

BRIEF DESCRIPTION OF DRAWINGS

In drawings which illustrate specific embodiments of the invention, but which should not be construed as restricting the spirit or scope of the invention in any way.

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Recent advances in knowledge (Freeman S., et al. in Bone conduction experiments in animals—evidence for a non-osseous mechanism, *Hearing Research* 146 (2000) 72-80) demonstrate a hitherto unknown route for sound waves to reach the inner ear via the brain and fluids inside the skull. The subject invention involves receiving external sound waves and imparting corresponding mechanical vibrations to the dura mater which travel as waves in the fluids inside the skull to stimulate the inner ear.

In one embodiment, the subject invention relates to a device which can be implanted in the head of a mammal and can impart vibrations corresponding to sound waves external to the head to the dura mater of the mammal. The mammal can be a human being.

In another embodiment, the invention relates to a device which can be implanted in the head of a mammal and can impart vibrations corresponding to sound waves external to the head to a moveable bone disc cut free from the skull that contacts the dura mater of the mammal. The mammal can be a human being.

In a further embodiment, the invention relates to a surgically implantable apparatus including:

(a) a microphone which receives sound waves and converts them to electrical signals;

(b) a transducer which converts the electrical signals to mechanical vibrations;

(c) a bracket which attaches to the skull over the mastoid cavity and supports the transducer;

(d) a member which transfers the mechanical vibrations to a moveable bone disc cut free from the skull that contacts the dura mater of the interior of the skull according to vibrations transmitted by the member.

In the embodiment described immediately above, the microphone receives and converts external sound waves to electrical signals. These electrical signals are conducted to the transducer on the bracket. The transducer converts the electrical signals to corresponding mechanical vibrations which are transmitted through the member to a moveable bone disc cut free from the skull that contacts the dura mater of the interior of the skull according to vibrations transmitted by the member. The mechanical vibrations imparted to the dura mater propagate as traveling waves through the brain and fluids inside the skull to the inner ear through channels presumed to be the vestibular and cochlear aqueduct and the perineural spaces.

There exist several alternative embodiments which modify the embodiment discussed immediately above. In one alternative embodiment the bracket is attached to the skull in an area other than the mastoid cavity of the human, where the skull is close to the brain and is not separated by other structures such as the frontal sinus, or intracranial venous sinuses.

In another alternative embodiment the member contacts a pad which contacts a bone disc contacting the dura mater and the pad transmits mechanical vibrations from the member to the bone disc.

In a further alternative embodiment the transducer contacts a bone disc contacting the dura mater and transmits vibrations to the bone disc directly.

In yet another alternative embodiment the member contacts the dura mater and transmits vibrations to the dura mater.

In yet a further alternative embodiment the member contacts a pad which contacts the dura mater and transmits vibrations from the member to the dura mater.

In yet a further alternative embodiment the transducer contacts the dura mater and transmits vibrations to the dura mater directly.

In still another alternative embodiment, the transducer contacts directly the dura mater.

All of the preceding embodiments may additionally incorporate one or more of the following elements: signal processing electronics for processing the electrical signals from the microphone before the electrical signals are transmitted to the transducer, said signal processing electronics can be directed at improving the functionality of the apparatus as a hearing aid, as a tinnitus masker, or as both a hearing aid and a tinnitus masker; control electronics, such as switches; one or more energy storage elements, such as a battery; one or more transcutaneous energy transfer elements, such as an internal coil and external coil pair; one or more wireless receivers for receiving data; one or more wireless transmitters for transmitting data; one or more magnets, at least one of which may be located subcutaneously, to facilitate alignment of internal and external portions of the apparatus; one or more wires for interconnecting elements; and one or more housings which may or may not be hermetically sealed, for containing elements.

A key aspect of the invention is imparting mechanical vibrations to the dura mater or to a floating bone disc that can contact the dura mater. It is possible for the vibrations to be imparted by a transducer directly, by a member connected to a transducer, or by a pad connected by a member to a transducer. In certain instances, the member and pad can be a single mechanism. In certain instances, the member can have a composite construction. In certain instances, the pad can have a composite construction. In certain instances, the transducer, member, or pad may be secured to the bone disc by adhesive, sewn, screw-type or clamp-type attachment. In certain instances, the transducer, member, or pad may contact and withdraw from the bone disc. In certain instances, the transducer, member, or pad may be secured to the dura mater by adhesive, sewn, screw-type or clamp-type attachment. In certain instances, the transducer, member, or pad may contact and withdraw from the dura mater.

Surgery provides a simple approach for installing an apparatus according to the invention. A short surgical incision (about 2½ inches) is made in the skin fold of the human being behind the ear, to expose the mastoid bone. A window is drilled in the mastoid bone, and landmarks in the medial wall of the mastoid cavity are identified by the surgeon. A safe site in which to uncover the dura mater is chosen by the surgeon. The device according to the invention is then installed by attaching the bracket to the skull of the human being and adjusting the member direction and length to thus bring the pad in position against the dura mater of the human being.

An alternative surgery cuts a bone disc out of the mastoid bone instead of drilling into the mastoid bone. The bone disc is left in place, but is free to impinge upon the dura mater. The device according to the invention is then installed by attaching the bracket to the skull of the human being and adjusting the member direction and length to thus bring the pad in position against the bone disc.

An advantage of the invention is that the surgery is simple, relatively non-invasive, avoids any vital structures and admits negligible risk of causing surgical damage to the human being. The invention also benefits from the ease of attachment of the device to different configurations such as (a) a totally internal configuration, (b) a partially implanted configuration, (c) a tinnitus masker, and (d) an attachment in combination with a cochlear implant.

Another advantage of the invention is that it can pick up external sound waves, and supply them in the form of mechanical vibrations to the dura mater and thus as traveling waves to the brain and fluids inside the skull. The traveling waves proceed through presumed channels such as the cochlear duct, the endolymphatic sac and perineural channels to impinge on the inner ear. Using this route to the inner ear of the human being provides a simple safe surgical approach to alleviating hearing problems of the human being.

A further advantage of the invention is that it may be practised in embodiments that are either fully or partially implanted in a human being. Embodiments that incorporate transcutaneous energy transfer elements may provide power to the transducer, microphone, internal battery, electronics or any combination of these from an external energy source, such as an external battery. Embodiments that incorporate one or more wireless receivers and one or more wireless transmitters may transmit signals corresponding to sound waves received by a microphone external to the head to a transducer attached subcutaneously to the skull. Embodiments that incorporate one or more wireless receivers and one or more wireless transmitters may also transmit data signals for adjusting the function of subcutaneous signal processing electronics or for manipulating switches that control operation of the device. The components of an embodiment of one such fully implantable hearing aid system is described in U.S. Pat. No. 6,358,281 BI, the contents of which are incorporated herein by reference.

The invention is also directed to a method for treating deafness or partial deafness in a human being. In one embodiment the method comprises transmitting vibrations to the human being's dura mater, wherein the vibrations correspond to sound waves external to the head of the human being. In a further embodiment, the method comprises transmitting vibrations to a bone disc resting on the human being's dura mater, wherein the vibrations correspond to sound waves external to the head of the human being. In yet a further embodiment, the method comprises coupling a transducer which converts electrical signals into mechanical vibrations to the human being's dura mater, converting sound waves external to the head of the human being into electrical signals, and transmitting the electrical signals to the transducer. In still a further embodiment the method comprises coupling a transducer which converts electrical signals into mechanical vibrations to a bone disc resting on the human being's dura mater, converting sound waves external to the head of the human being into electrical signals, and transmitting the electrical signals to the transducer.

The invention is also directed to a method for masking tinnitus in a human being. In one embodiment the method comprises transmitting vibrations to the human being's dura mater. In a further embodiment the method comprises transmitting vibrations to a bone disc resting on the human being's dura mater. In yet a further embodiment the method comprises coupling a transducer which converts electrical signals into mechanical vibrations to the human being's dura mater, generating electrical signals, and transmitting the electrical signals to the transducer. In still a further embodiment the method comprises coupling a transducer which converts electrical signals into mechanical vibrations to a bone disc resting on the human being's dura mater, generating electrical signals and transmitting the electrical signals to the transducer.

Embodiments of the invention can be used to treat deafness, partial deafness, tinnitus or a combination of these ailments. Embodiments of the invention can be used in association with a cochlear implant. Embodiments of the invention can be used in both ears of a person as a bilateral aid to hearing.

Figure 1A:
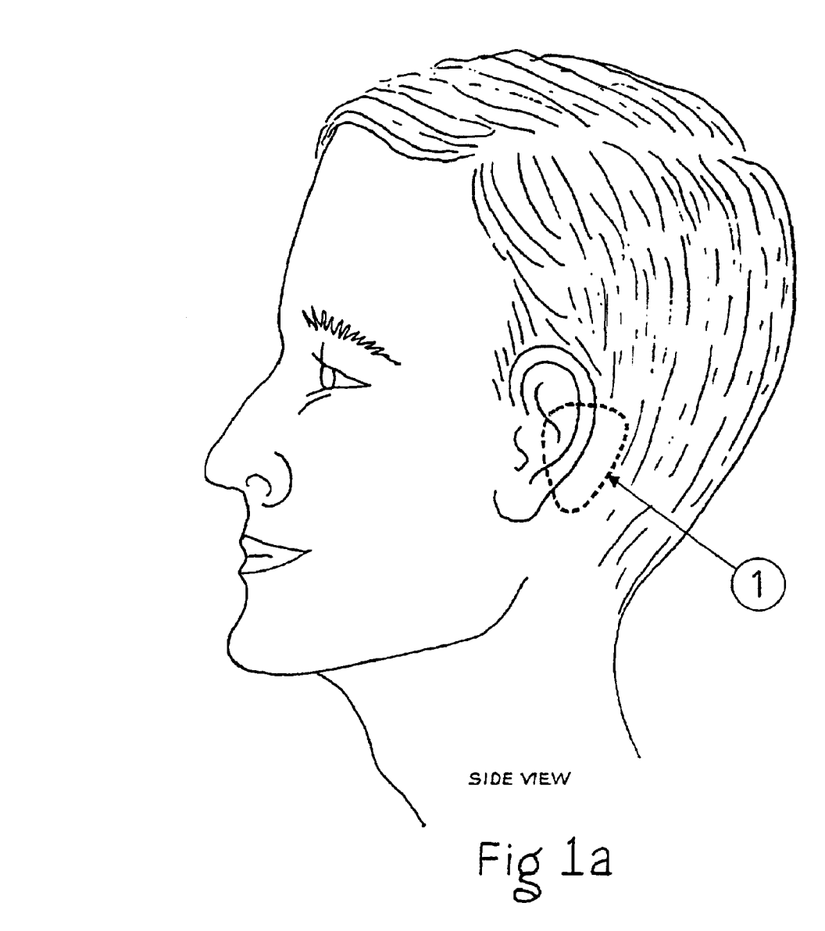
FIG. 1a illustrates an isometric view of the left side of the head of a human being with the mastoid cavity area outlined with a dotted line.
Figure 1B:
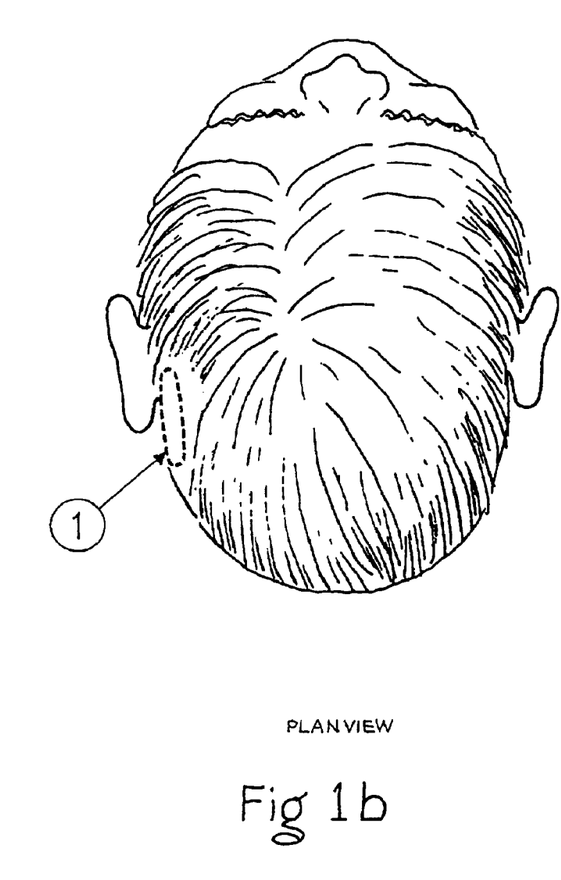
FIG. 1b illustrates an isometric view of the top of the head of a human being with the mastoid cavity area on the left side outlined with a dotted line.

FIG. 1a illustrates an isometric left side view of the head of a human being with the mastoid location 1 indicated in dotted lines. FIG. 1b illustrates an isometric plan view of the head with the mastoid location 1 indicated by dotted lines. The mastoid location 1 is a preferred, but not the only, location for implanting the device according to the invention. Apparatuses according to the invention may be made small and designed to work in the area of the mastoid air cells by taking advantage of commercially available microelectronics.

Figure 2:
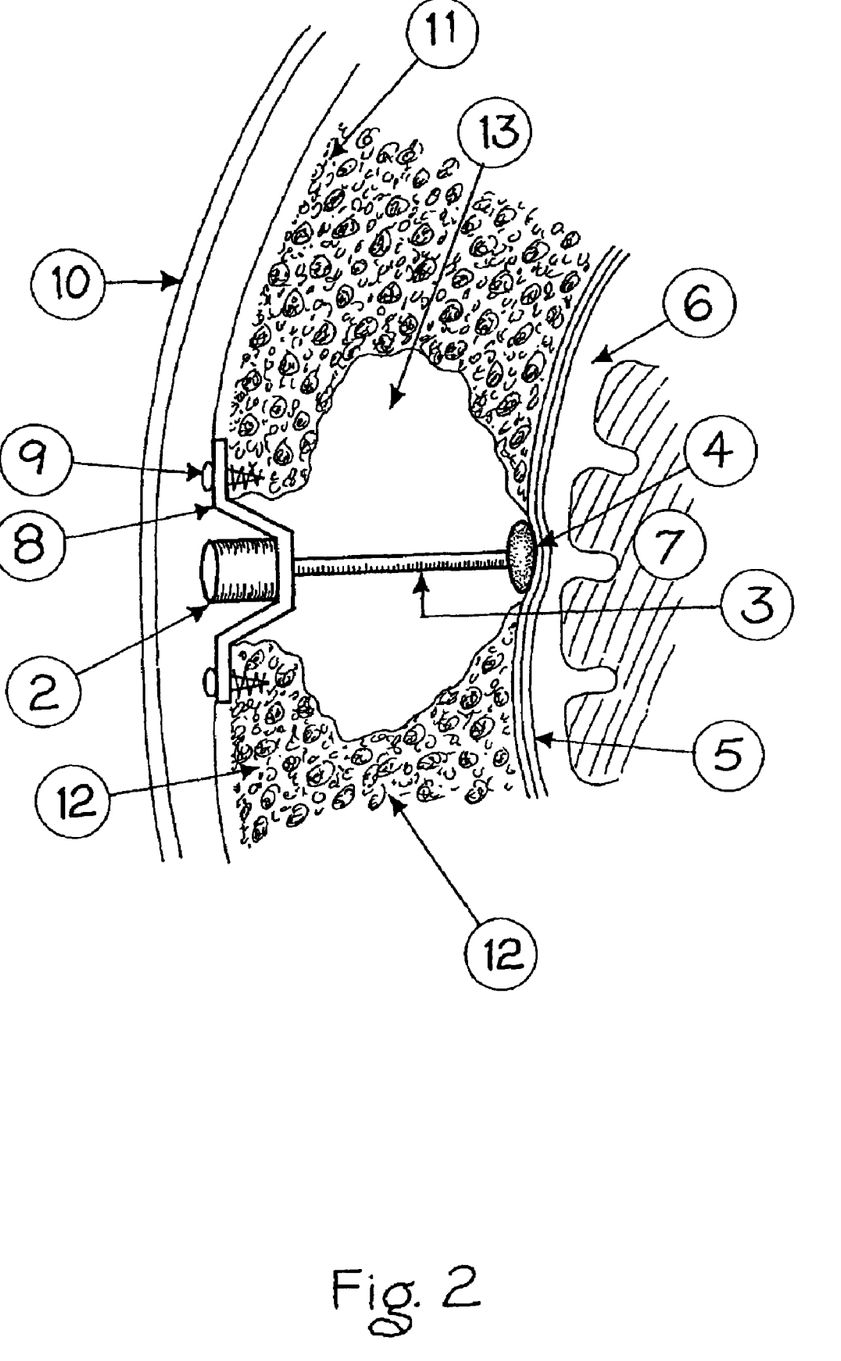
FIG. 2 illustrates a diagrammatic cross section of a first embodiment of the device in place in a horizontal section through the mastoid cavity behind the ear.

FIG. 2 illustrates an enlarged diagrammatic cross section of an embodiment of the device installed in a horizontal section through the mastoid cavity 13 behind the ear. FIG. 2 shows the device in place after surgical implantation. Electrical signals originate from a microphone (not shown and are transmitted to a transducer contained in a housing 2. The transducer produces mechanical vibrations according to the electrical signals that it receives. The mechanical vibrations are transmitted through the member 3 to a pad 4, which contacts the dura mater 5 of the human being. The pad transmits the vibrations to the dura mater 5. The vibrations travel through the fluids inside the skull 6 and brain as traveling waves to the inner ear. The transducer in its housing 2 is held in place on the surface of the mastoid 12 by a bracket 8 and screws 9. For completeness of illustration, some anatomical details are shown in FIG. 2, namely the skin 10, the bone of the skull 11 the surrounding mastoid air cells 12 and the mastoid cavity 13. It will be understood that the surgical cavity 13 shown in FIG. 2 has been enlarged for illustrative purposes and, in practice, is not as large as shown in FIG. 2. In practice, the cavity 13 is in the form of a hollow hemisphere, and of sufficient size to house the housing 2, member 3 and pad 4.

Figure 3:
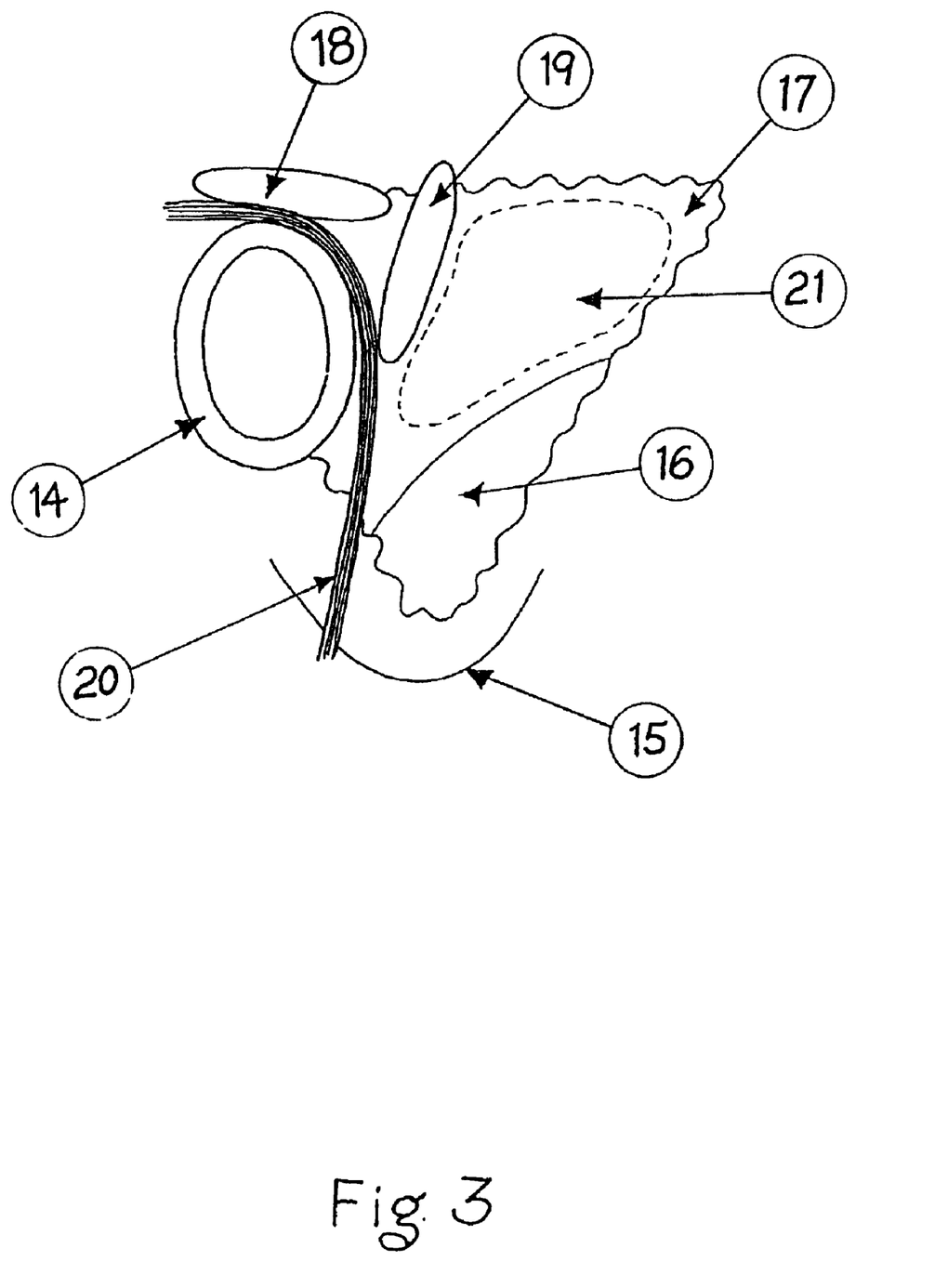
FIG. 3 illustrates a diagrammatic representation of the anatomy of the medial view of the external ear canal and the mastoid cavity.

FIG. 3 represents an enlarged view of the medial wall of the surgical area of the left ear and surroundings in diagrammatic form. To clarify the landmarks, and for illustrative purposes, it is expanded as if there has been some removal of bone. The external auditory canal 14 is shown and also the mastoid bone tip 15, the area of the lateral sinus 16, the sino-dural angle 17, the horizontal semicircular canal 18, the posterior semicircular canal 19 and the facial nerve 20. An area 21 has been outlined in dotted lines in which the dura mater may be exposed by a surgeon skilled in the art, with considerable safety, thus providing access of the pad 4 of the device to the dura mater without compromising any other significant anatomical structures.

Figure 4:
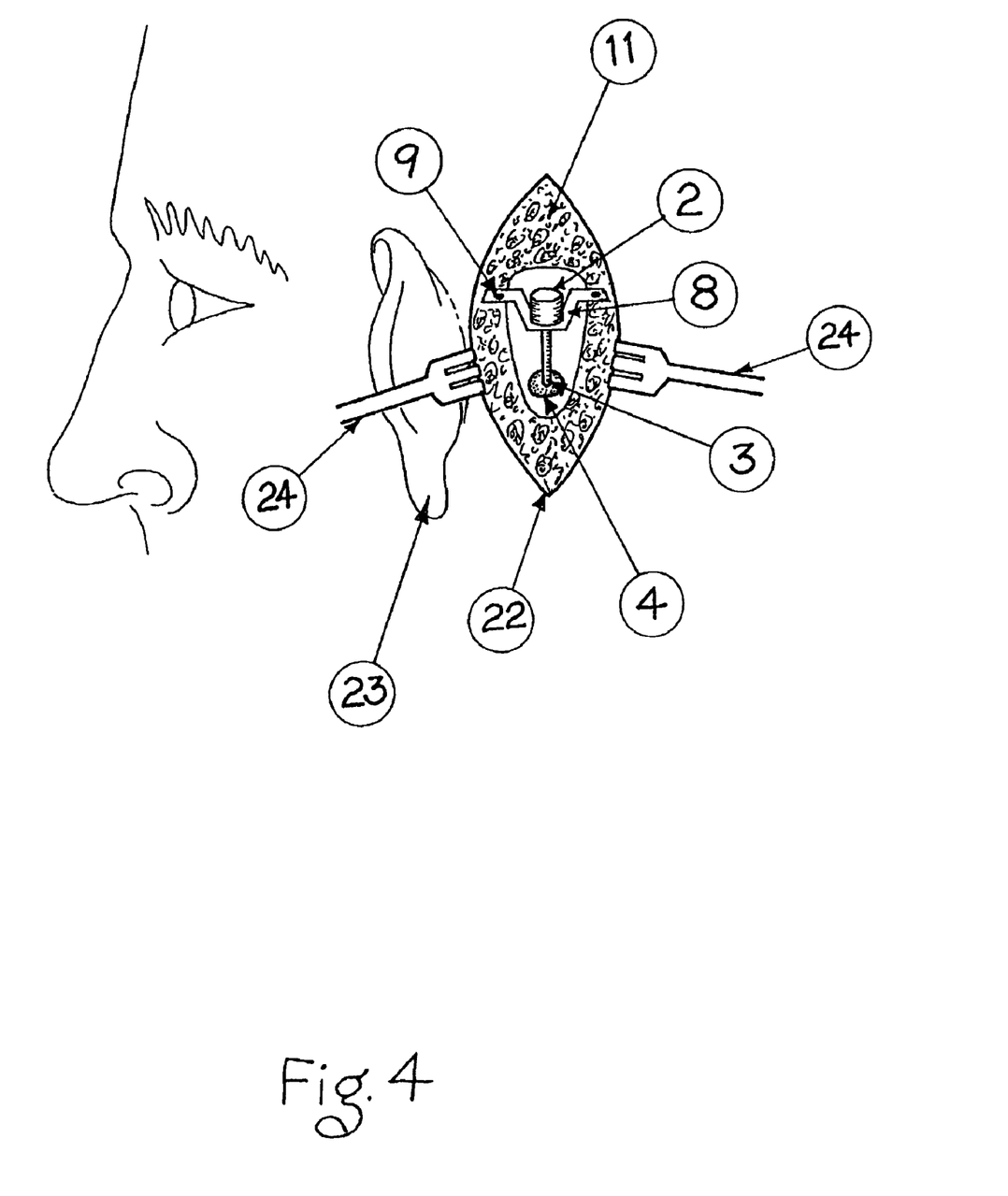
FIG. 4 illustrates an isometric left side view of the head of a human being and a diagrammatic representation of the surgical approach to the mastoid cavity and dura mater with the preferred embodiment of the implant in place. The device has been rotated slightly with the pad down to clarify the view of it.

FIG. 4 illustrates an isometric left side view of the head of a human being and the surgical approach to the mastoid cavity and dura mater with the preferred embodiment of the implant in place. FIG. 4 specifically illustrates the application with a vertical surgical incision 22 made behind the left ear 23 of the human being. The skin is retracted with retractors 24 to expose the device in its surgical position. For clarity, the device is shown rotated slightly down to show the bracket 8 and screws 9, which hold the bracket to the bone of the skull 11 and the transducer in its hermetically sealed housing 2. Also shown are the member 3 and the pad 4 against the dura mater. It is understood that the member 3 and pad 4 can be a single unit.

Figure 5:
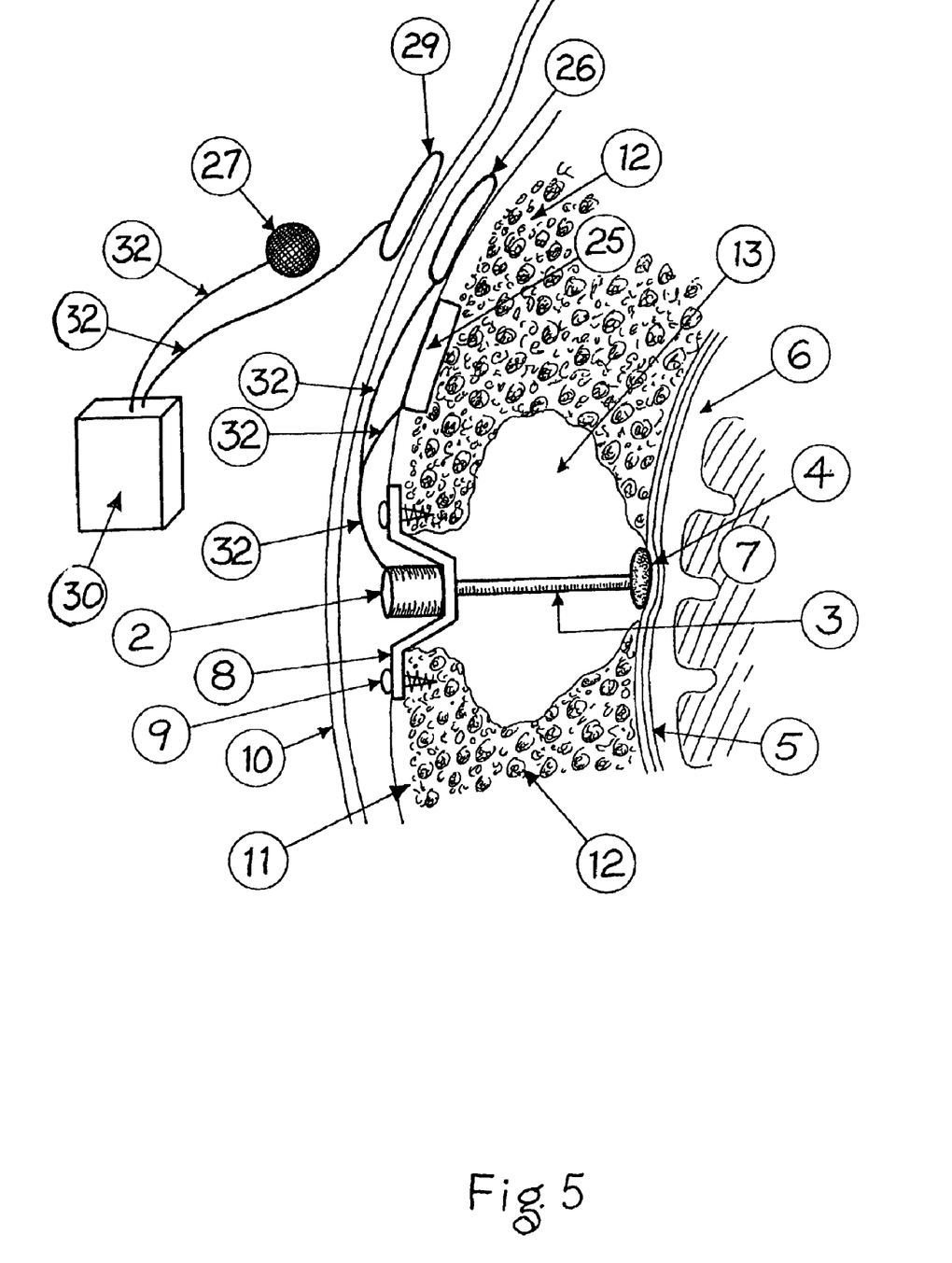
FIG. 5 illustrates a partial section view of the left side of the human being's head with the partially implantable aid consisting of a second embodiment of the device connected to a housing and electronics implanted in the skull and a coil placed in a subcutaneous position over the skull.

FIG. 5 shows in enlarged cross-section view one of the embodiments of the invention. In particular, FIG. 5 illustrates a partial section-view of the left side of the human being's head with the partially implantable hearing aid consisting of the preferred embodiment of the device connected to a housing and electronics implanted in the skull and a radio frequency coil 26 placed in a subcutaneous position over the skull of the human being. This coil 26 communicates with an external coil 29 by electromagnetic waves. Coil 29 is attached to a housing 30 which contains a battery and signal processing electronics, and also a microphone 27. To accommodate the implantable device (2, 3 and 4), the mastoid cavity 13 has been enlarged by the surgeon by drilling the mastoid air cells. The transducer is shown in its hermetically sealed housing 2 on a bracket 8 held by screws 9 to the exterior bone of the skull 11 of the human being. A member 3 connects the housing 2 to the pad 4, which is touching the dura mater 5. The electronics for the transducer in the housing 2 are contained in a hermetically sealed housing 25 embedded in the surface of the skull. These electronics communicate with the RF coil 26 under the skin 10 and allow communication with and power delivery by the external components. These external components comprise an external microphone 27, which receives external sound waves, and appropriate electronics, battery and switches housed in a housing 30 which in turn are connected to external RF coil 29. In operation the microphone 27 receives and converts external sound waves to electrical signals which are subjected to electronic signal processing by the electronics in housing 30 and are communicated by the RF links to the device at its transducer in housing 2, which converts the electrical signals to corresponding mechanical vibrations, which are then transmitted by the member 3 to the pad 4, and then the dura mater 5, cerebrospinal fluid 6 and brain 7 whereby it reaches the inner ear of the human being. The transducer and all the electronic parts and the microphone 27 are joined together by wires 32.

Figure 6:
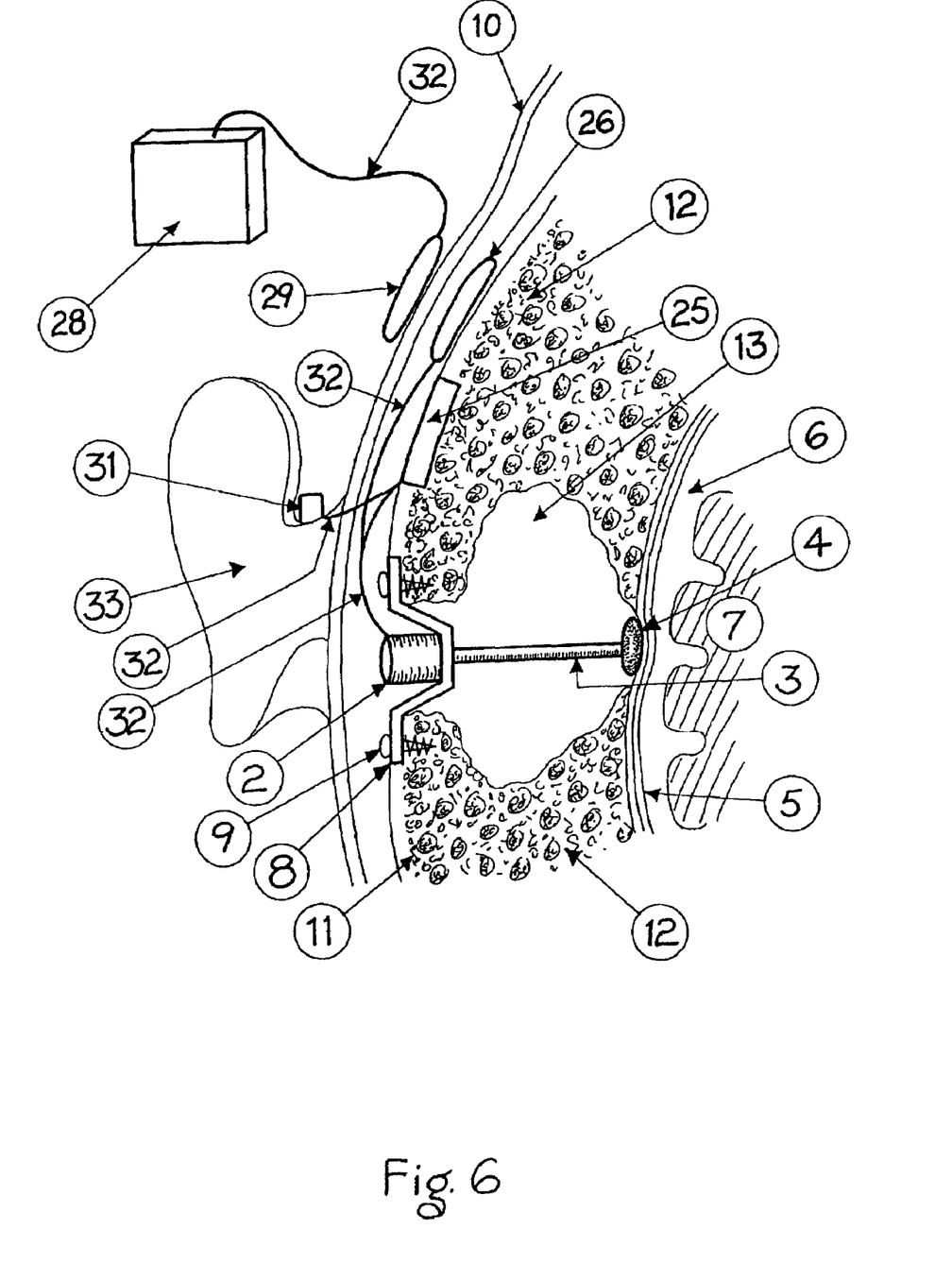
FIG. 6 illustrates an alternative third embodiment of the invention with an internal microphone, an internal battery and electronics, and a coil to allow recharging the battery and switching control of the electronics through an external apparatus.

FIG. 6 shows a further embodiment of the invention with an internal rather than external microphone, an internal battery and electronics, and a coil to allow of recharging the battery and switching control of the electronics through an external apparatus. As seen in FIG. 6, the device is totally implanted and the external electronics in housing 28 merely serve to recharge the internal battery and adjust the internal electronic switching 25 via an external coil 29 and an internal coil 26 is located under the human being's skin 10. The microphone 31 is located internally and in one embodiment it is positioned in the external ear canal 33. The microphone 31 receives and converts external sound waves to electrical signals which are processed in the electronics that are contained within the hermetically sealed housing 25 and transmitted to the transducer in housing 2 that is held in the skull 11 by a bracket 8 and screws 9. The transducer converts the electrical signals to corresponding mechanical vibrations which are transmitted through the member 3 which passes through the mastoid cavity 13, which has been surgically enlarged by excision of some mastoid air cells 12, and then to the pad 4, which impinges the dura mater 5. These components drive mechanical waves through the dura mater 5 to the cerebrospinal fluid 6 and brain 7 and ultimately to the inner ear. The transducer and all the electronic parts and the microphone are joined together by wires 32 as indicated.

Figure 7:
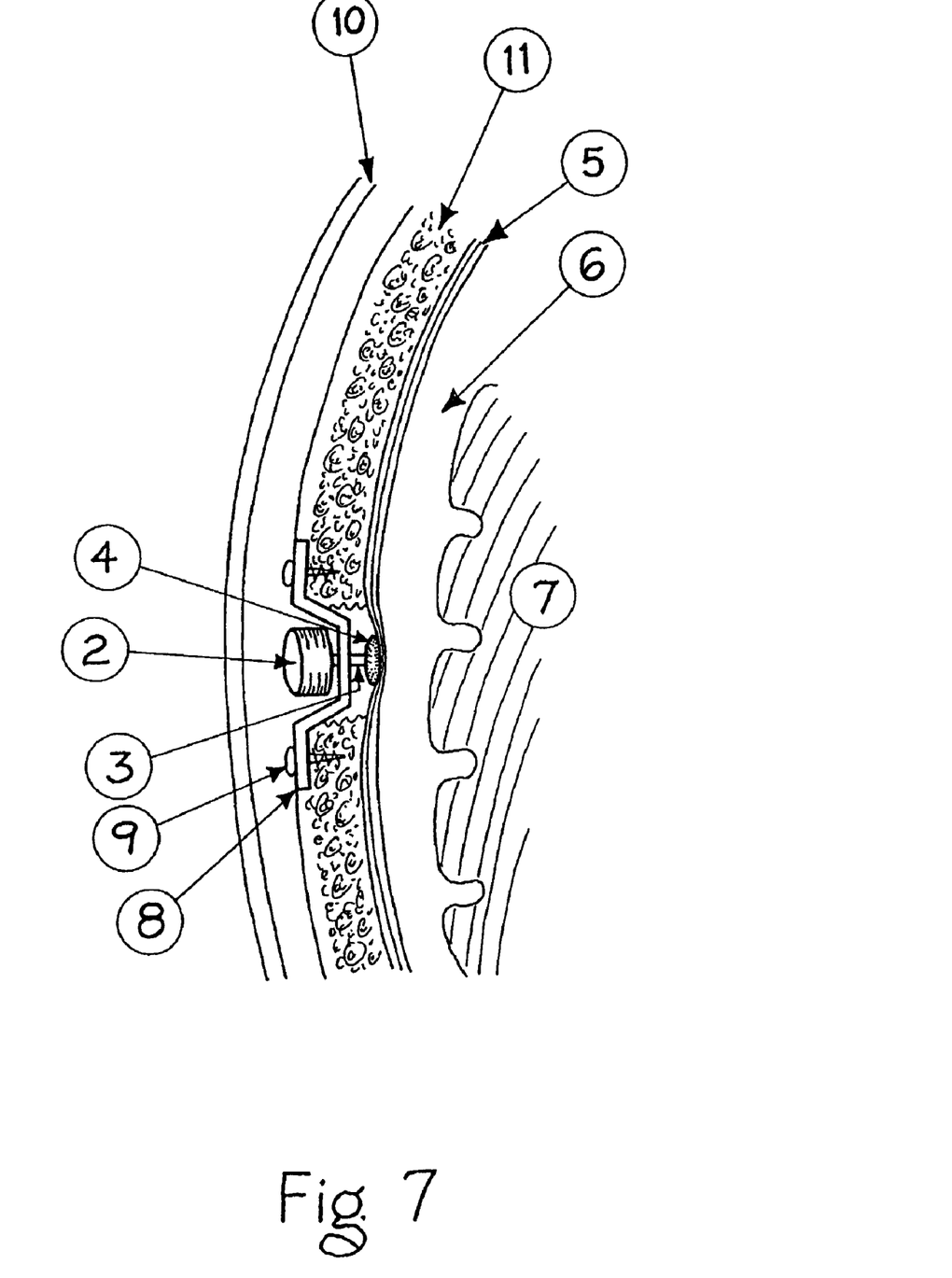
FIG. 7 illustrates a fourth embodiment in which the device is placed through the skull to make contact directly with the dura mater, without crossing the mastoid or other air space.

FIG. 7 illustrates yet a further embodiment of the invention in which the device is placed within a selected part of the skull other than the mastoid area or the frontal sinus or the intracranial venous sinuses, such that the dura mater 5 is directly within the skull 11 underlying the surgical excavation and not separated by any other structure. FIG. 7 shows the key elements of the device placed in such a location under the skin 10 and in a cavity surgically constructed in the skull 11. In this case the transducer in housing 2 is connected to a member 3 and this in turn to a pad 4. The bracket 8 is affixed to the skull by screws 9 and is shallower to accommodate this location and is set beneath the skin 10. Mechanical vibrations are transferred from the transducer in housing 2 down the member 3 to the pad 4 and then transferred through the dura mater 5 to the cerebrospinal fluid 6 and the brain 7 as discussed above.

Figure 8:
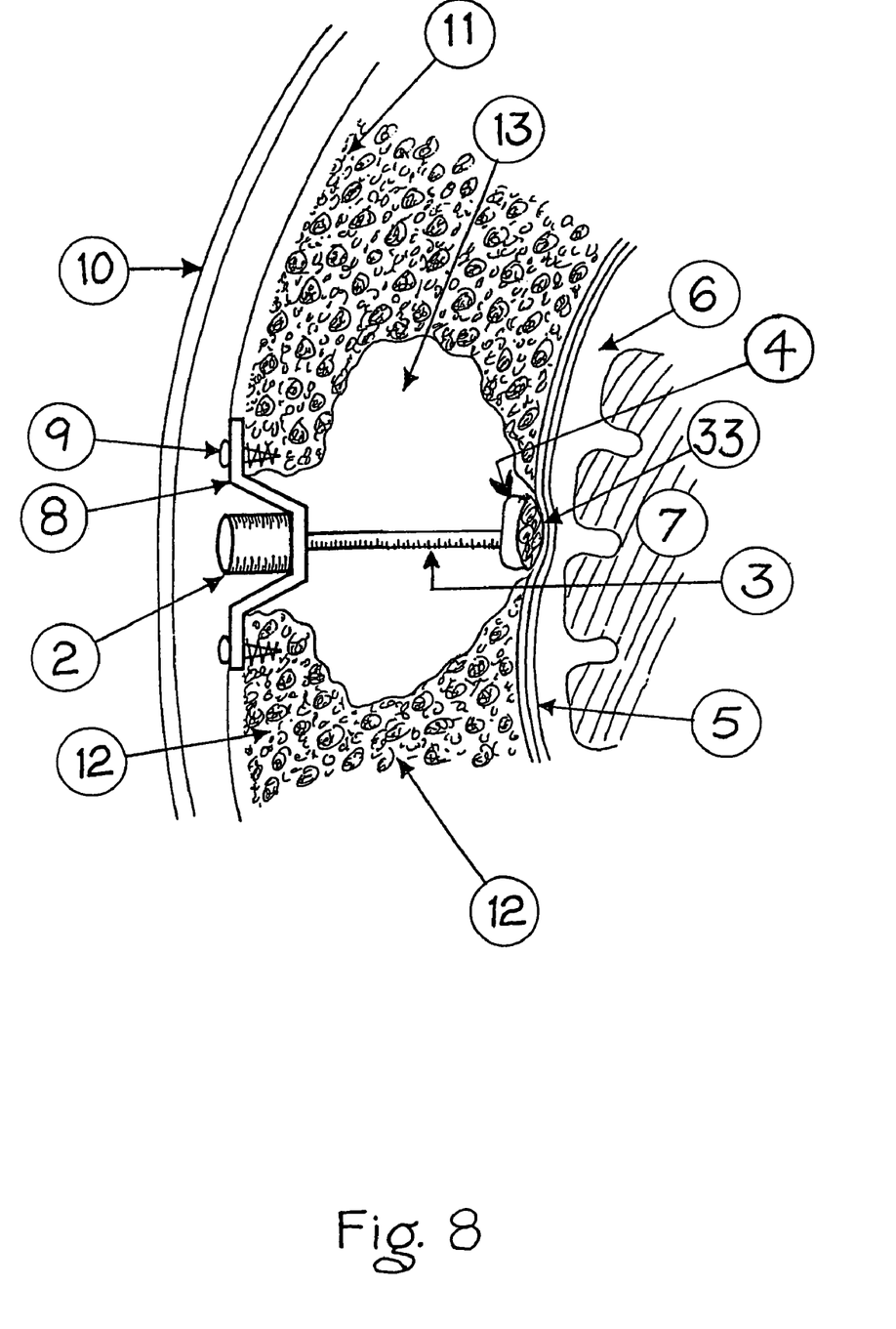
FIG. 8 illustrates a diagrammatic cross section of a fifth embodiment of the device in place in a horizontal section through the mastoid cavity behind the ear.

FIG. 8 illustrates an enlarged diagrammatic cross section of a further embodiment of the device installed in a horizontal section through the mastoid cavity 13 behind the ear. FIG. 8 shows the device in place after surgical implantation. Electrical signals originate from a microphone (not shown and are transmitted to a transducer contained in a housing 2. The transducer produces mechanical vibrations according to the electrical signals that it receives. The mechanical vibrations are transmitted through the member 3 to a pad 4, which contacts a bone disc 33 which rests on the dura mater 5 of the human being. The pad 4 transmits the vibrations to the bone disc 33 which impinges the dura mater. The vibrations travel through the fluids inside the skull 6 and brain as waves to the inner ear. The transducer in its housing 2 is held in place on the surface of the mastoid 12 by a bracket 8 and screws 9. For completeness of illustration, some anatomical details are shown in FIG. 8, namely the skin 10, the bone of the skull 1 the surrounding mastoid air cells 12 and the mastoid cavity 13. It will be understood that the surgical cavity 13 shown in FIG. 8 has been enlarged for illustrative purposes and, in practice, is not as large as shown in FIG. 8. In practice, the cavity 13 is in the form of a hollow hemisphere, and of sufficient size to house the housing 2, member 3 and pad 4.

Figure 9A:
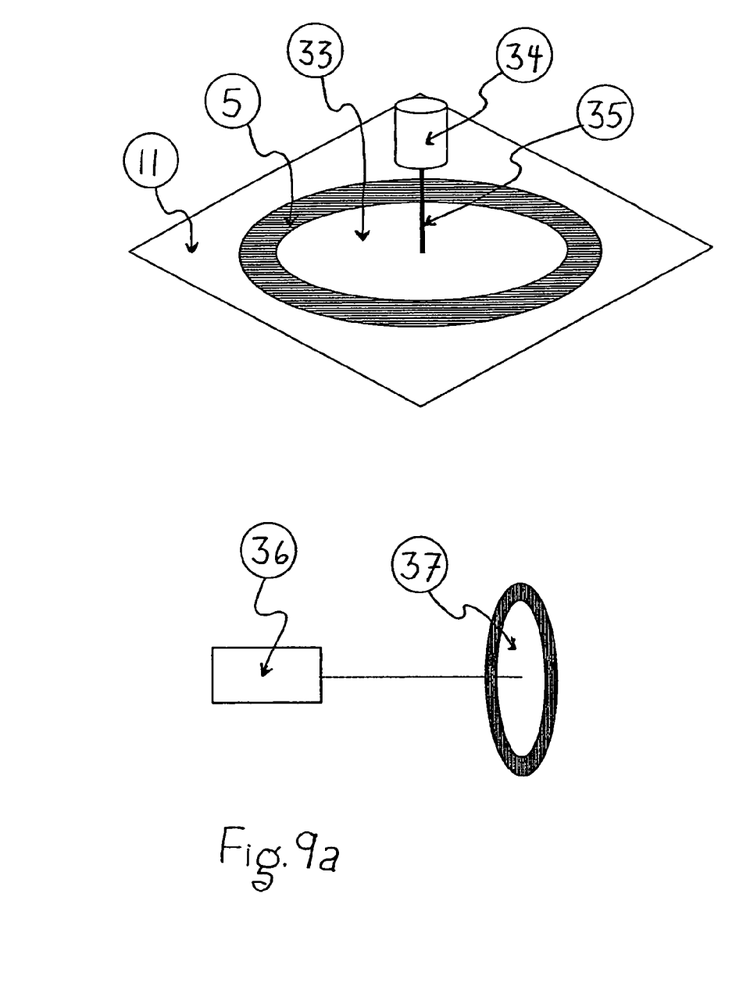
FIG. 9a illustrates a simplified schematic representation of an experimental apparatus used to measure vibrations incident on the inner ear in response to vibrations applied to a dura mater contacting bone island.

FIG. 9a illustrates a simplified schematic representation of an experimental apparatus used to measure vibrations incident on the inner ear in response to vibrations applied to a dura mater contacting bone island. A bone island 33 cut free from the mastoid bone of the skull 11 rests on the dura mater 5. The dura mater 5 is exposed where bone has been removed to free the bone island 33. A BAHA-Cordell stimulator 34, which is a transducer that converts electrical energy to mechanical vibrations, is coupled to a member 35 which is affixed to the bone island 33. A laser doppler vibrometer 36 measures movement of the round window membrane 37. Movement of the round window membrane 37 indicates pressure waves incident on the inner ear.

Figure 9B:
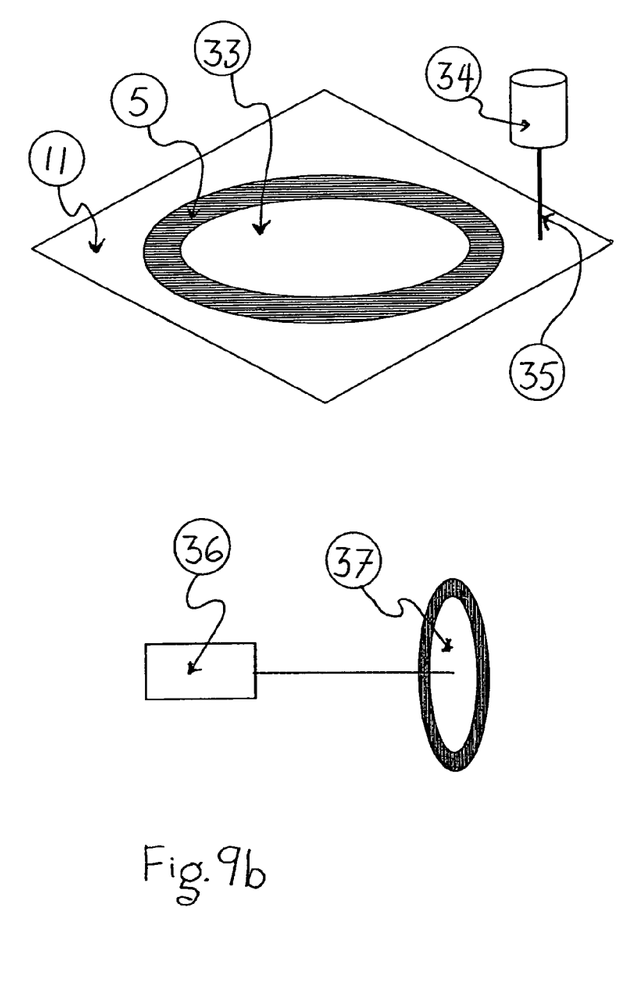
FIG. 9b illustrates a simplified schematic representation of an experimental apparatus used to measure vibrations incident on the inner ear in response to vibrations applied to the mastoid bone of the skull.

FIG. 9b illustrates a simplified schematic representation of an experimental apparatus used to measure vibrations incident on the inner ear in response to vibrations applied the mastoid bone of the skull. A BAHA-Cordell stimulator 34 is coupled to a member 35 which is affixed to the mastoid bone of the skull 11. A laser doppler vibrometer 36 measures movement of the round window membrane 37.

Experimental apparatuses according to those shown in FIG. 9a and FIG. 9b were used in an experiment to validate in principle the utility of the subject invention. An adult male patient who was planned to have cochlea implant surgery agreed to allow testing of the principle of the subject invention during the surgery. A postauricular incision was made and the mastoid cavity was widely exposed using an operative microscope. A window was opened anteriorly through the facial recess into the middle ear so that the round window membrane could be seen. A bone island was cut free from the mastoid bone of the skull. A member was screwed onto the bone island and coupled to a BAHA-Cordell stimulator. The BAHA-Cordell stimulator was used to apply a sine tone vibration to the bone island. The frequency of the sine tone vibration was varied across a range from 500 Hz to 4000 Hz. At various frequencies a laser doppler vibrometer was used to measure movement of the round window membrane. The member was removed from the bone island and screwed onto the mastoid bone of the skull at a location adjacent to the bone island. The BAHA-Cordell stimulator was used to apply a sine tone vibration to the mastoid bone of the skull. The frequency of the sine tone vibration was varied across a range from 500 Hz to 4000 Hz. At various frequencies a laser doppler vibrometer was used to measure movement of the round window membrane.

Figure 10:
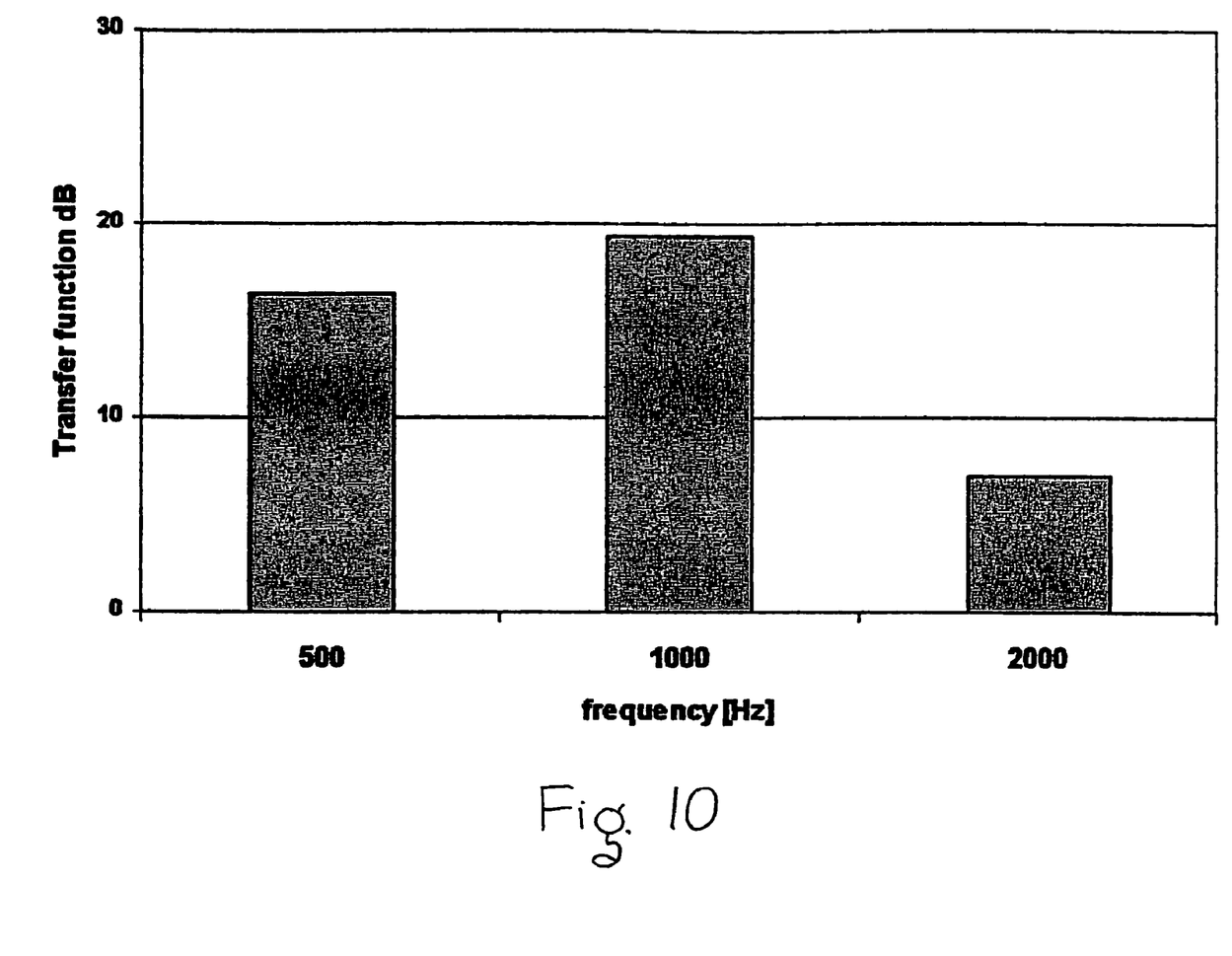
FIG. 10 illustrates the transfer function improvement for vibrations transmitted via the bone island to the round window versus vibrations transmitted via the mastoid bone of the skull to the round window.

FIG. 10 illustrates the transfer function improvement for vibrations transmitted via the bone island to the round window versus vibrations transmitted via the mastoid bone of the skull to the round window. The graph indicates that vibrations applied to the bone island, and hence conducted via the dura mater, stimulate the inner ear much more than vibrations applied to the mastoid bone of the skull.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A method for treating deafness or partial deafness in a human being comprising transmitting vibrations to a bone disc resting on the human being's dura mater, wherein the vibrations correspond to sound waves external to the head of the human being.

2. A method for treating deafness or partial deafness in a human being comprising:
   (a) coupling a transducer which converts electrical signals into mechanical vibrations to a bone disc resting on the human being's dura mater;
   (b) converting sound waves external to the head of the human being into electrical signals; and,
   (c) transmitting the electrical signals to the transducer.

3. The method according to claim 2 comprising the further step of processing the electrical signals before transmitting them to the transducer.

4. The method according to claim 2 comprising the further step of securing the transducer to the skull.

5. A method for masking tinnitus in a human being comprising transmitting vibrations to a bone disc resting on the human being's dura mater.

* * * * *